(12) United States Patent
Hausen et al.

(10) Patent No.: US 9,155,536 B1
(45) Date of Patent: Oct. 13, 2015

(54) CIRCULAR STAPLER

(75) Inventors: Bernard A. Hausen, Redwood City, CA (US); Bryan D. Knodel, Flagstaff, AZ (US)

(73) Assignee: Cardica, Inc., Redwood City, CA (US)

( * ) Notice: Subject to any disclaimer, the term of this patent is extended or adjusted under 35 U.S.C. 154(b) by 563 days.

(21) Appl. No.: 13/094,814

(22) Filed: Apr. 26, 2011

(51) Int. Cl.
| | |
|---|---|
| A61B 17/04 | (2006.01) |
| A61B 17/10 | (2006.01) |
| A61B 17/068 | (2006.01) |
| A61B 17/115 | (2006.01) |

(52) U.S. Cl.
CPC ........... *A61B 17/068* (2013.01); *A61B 17/1155* (2013.01)

(58) Field of Classification Search
CPC .......................... A61B 17/068; A61B 17/1155
USPC ........................................... 227/175.1–182.1
See application file for complete search history.

(56) References Cited

U.S. PATENT DOCUMENTS

| | | |
|---|---|---|
| 2,127,665 A | 8/1938 | Leslie |
| 3,581,551 A | 6/1971 | Wilkinson |
| 3,650,453 A | 3/1972 | Smith, Jr. |
| 3,675,688 A | 7/1972 | Bryan et al. |
| 3,717,294 A | 2/1973 | Green |
| 3,837,555 A | 9/1974 | Green |
| 3,899,914 A | 8/1975 | Akiyama |
| 3,955,581 A | 5/1976 | Spasiano et al. |
| 4,043,504 A | 8/1977 | Hueil et al. |
| 4,086,926 A | 5/1978 | Green et al. |
| 4,127,227 A | 11/1978 | Green |
| 4,228,895 A | 10/1980 | Larkin |
| 4,275,813 A | 6/1981 | Noiles et al. |
| 4,475,679 A | 10/1984 | Fleury, Jr. |
| 4,523,707 A | 6/1985 | Blake, III et al. |
| 4,556,058 A | 12/1985 | Green |
| 4,589,416 A | 5/1986 | Green |
| 4,633,861 A | 1/1987 | Chow et al. |
| 4,655,222 A | 4/1987 | Florez et al. |
| 4,719,917 A | 1/1988 | Barrows et al. |

(Continued)

FOREIGN PATENT DOCUMENTS

| | | |
|---|---|---|
| EP | 1238634 | 9/1994 |
| EP | 1464287 | 10/2004 |

(Continued)

OTHER PUBLICATIONS

Gong, Shao W., "Perfectly flexible mechanism and integrated mechanism system design", *Mechanism and Machine Theory* 39 (2004), (Nov. 2004),1155-1174.

Lim, Jonas J., et al., "A review of mechanism used in laparascopic surgical instruments", *Mechanism and Machine Theory* 38, (2003),1133-1147.

(Continued)

*Primary Examiner* — Robert Long
(74) *Attorney, Agent, or Firm* — Womble Carlyle Sandridge & Rice LLP

(57) ABSTRACT

An exemplary circular stapler may include an anvil; a staple holder connected to the anvil; and a feeder belt ring held within the staple holder, the feeder belt ring including staples frangibly affixed thereto. An exemplary surgical method for treating tissue may include possessing an anvil, a staple holder connected to the anvil, and a feeder belt ring held within the staple holder, the feeder belt ring including a plurality of staples frangibly affixed thereto; clamping tissue between the anvil and staple holder; and sequentially deforming and then breaking from the feeder belt ring at least two staples.

20 Claims, 3 Drawing Sheets

(56) References Cited

U.S. PATENT DOCUMENTS

| | | | |
|---|---|---|---|
| 4,762,260 A | 8/1988 | Richards et al. | |
| 4,805,617 A * | 2/1989 | Bedi et al. | 606/220 |
| 4,930,674 A * | 6/1990 | Barak | 227/179.1 |
| 4,969,591 A | 11/1990 | Richards et al. | |
| 4,978,049 A | 12/1990 | Green | |
| 5,139,513 A * | 8/1992 | Segato | 606/219 |
| 5,156,315 A | 10/1992 | Green et al. | |
| 5,170,925 A | 12/1992 | Madden et al. | |
| 5,192,288 A | 3/1993 | Thompson et al. | |
| 5,222,963 A * | 6/1993 | Brinkerhoff et al. | 606/153 |
| 5,242,457 A | 9/1993 | Akopov et al. | |
| 5,250,058 A * | 10/1993 | Miller et al. | 606/154 |
| 5,269,792 A | 12/1993 | Kovac et al. | |
| 5,307,976 A | 5/1994 | Olson et al. | |
| 5,413,272 A | 5/1995 | Green et al. | |
| 5,415,334 A | 5/1995 | Williamson, IV et al. | |
| 5,456,400 A | 10/1995 | Shichman et al. | |
| 5,476,206 A | 12/1995 | Green | |
| 5,507,776 A | 4/1996 | Hempel | |
| 5,527,319 A | 6/1996 | Green et al. | |
| 5,547,117 A | 8/1996 | Hamblin et al. | |
| 5,547,474 A | 8/1996 | Kloeckl et al. | |
| 5,553,765 A | 9/1996 | Knodel et al. | |
| 5,620,289 A | 4/1997 | Curry | |
| 5,626,585 A | 5/1997 | Mittelstadt et al. | |
| 5,630,541 A | 5/1997 | Williamson, IV et al. | |
| 5,655,698 A | 8/1997 | Yoon | |
| 5,662,260 A | 9/1997 | Yoon | |
| 5,692,668 A | 12/1997 | Schulze et al. | |
| 5,797,931 A * | 8/1998 | Bito et al. | 606/151 |
| 5,810,457 A * | 9/1998 | Felsenthal et al. | 312/6 |
| 5,810,855 A | 9/1998 | Rayburn et al. | |
| 5,816,471 A | 10/1998 | Plyley et al. | |
| 5,833,695 A * | 11/1998 | Yoon | 606/139 |
| 5,855,311 A | 1/1999 | Hamblin et al. | |
| 5,860,581 A * | 1/1999 | Robertson et al. | 227/179.1 |
| 5,871,135 A | 2/1999 | Williamson, IV et al. | |
| 5,875,538 A | 3/1999 | Kish et al. | |
| 5,894,979 A | 4/1999 | Powell | |
| 5,904,697 A * | 5/1999 | Gifford et al. | 606/155 |
| 5,906,625 A * | 5/1999 | Bito et al. | 606/142 |
| 5,918,791 A | 7/1999 | Sorrentino et al. | |
| 5,964,774 A | 10/1999 | McKean et al. | |
| 5,974,918 A * | 11/1999 | Nakagawa et al. | 81/434 |
| 5,976,159 A * | 11/1999 | Bolduc et al. | 606/142 |
| 6,110,187 A * | 8/2000 | Donlon | 606/151 |
| 6,193,129 B1 * | 2/2001 | Bittner et al. | 227/180.1 |
| 6,264,087 B1 | 7/2001 | Whitman | |
| 6,306,149 B1 | 10/2001 | Meade | |
| 6,391,038 B2 | 5/2002 | Vargas et al. | |
| 6,419,682 B1 | 7/2002 | Appleby et al. | |
| 6,443,973 B1 | 9/2002 | Whitman | |
| 6,478,804 B2 | 11/2002 | Vargas et al. | |
| 6,592,597 B2 | 7/2003 | Grant et al. | |
| 6,602,252 B2 | 8/2003 | Mollenauer | |
| 6,716,232 B1 | 4/2004 | Vidal et al. | |
| 6,779,959 B1 * | 8/2004 | Yang | 411/443 |
| 6,817,508 B1 | 11/2004 | Racenet | |
| 6,843,403 B2 | 1/2005 | Whitman | |
| 7,025,747 B2 | 4/2006 | Smith | |
| 7,055,730 B2 | 6/2006 | Ehrenfels et al. | |
| 7,097,089 B2 | 8/2006 | Marczyk | |
| 7,111,768 B2 | 9/2006 | Cummins et al. | |
| 7,128,253 B2 | 10/2006 | Mastri et al. | |
| 7,140,527 B2 | 11/2006 | Ehrenfels et al. | |
| 7,168,604 B2 | 1/2007 | Milliman et al. | |
| 7,172,104 B2 | 2/2007 | Scirica et al. | |
| 7,179,267 B2 | 2/2007 | Nolan et al. | |
| 7,207,471 B2 | 4/2007 | Heinrich et al. | |
| 7,213,736 B2 | 5/2007 | Wales et al. | |
| 7,217,285 B2 * | 5/2007 | Vargas et al. | 623/1.36 |
| 7,225,963 B2 | 6/2007 | Scirica | |
| 7,225,964 B2 | 6/2007 | Mastri et al. | |
| 7,234,624 B2 | 6/2007 | Gresham et al. | |
| 7,238,195 B2 | 7/2007 | Viola | |
| 7,258,262 B2 | 8/2007 | Mastri et al. | |
| 7,401,720 B1 | 7/2008 | Durrani | |
| 7,434,715 B2 | 10/2008 | Shelton, IV et al. | |
| 7,438,209 B1 * | 10/2008 | Hess et al. | 227/180.1 |
| 7,467,740 B2 | 12/2008 | Shelton, IV et al. | |
| 7,497,865 B2 | 3/2009 | Willis et al. | |
| 7,506,791 B2 | 3/2009 | Omaits et al. | |
| 7,517,356 B2 | 4/2009 | Heinrich | |
| 7,588,177 B2 | 9/2009 | Racenet | |
| 7,604,151 B2 | 10/2009 | Hess et al. | |
| 7,635,073 B2 | 12/2009 | Heinrich | |
| 7,635,373 B2 | 12/2009 | Ortiz | |
| 7,641,432 B2 | 1/2010 | Lat et al. | |
| 7,644,848 B2 | 1/2010 | Swayze et al. | |
| 7,918,376 B1 * | 4/2011 | Knodel et al. | 227/175.1 |
| 7,954,683 B1 | 6/2011 | Knodel et al. | 227/175.1 |
| 7,963,432 B2 * | 6/2011 | Knodel et al. | 227/175.1 |
| 7,988,026 B2 * | 8/2011 | Knodel et al. | 227/175.1 |
| 8,070,034 B1 * | 12/2011 | Knodel | 227/176.1 |
| 8,070,036 B1 | 12/2011 | Knodel | 227/178.1 |
| 8,096,457 B1 * | 1/2012 | Manoux et al. | 227/175.1 |
| 8,163,010 B1 | 4/2012 | Hausen et al. | 623/2.32 |
| 8,220,690 B2 * | 7/2012 | Hess et al. | 227/181.1 |
| 8,225,980 B1 | 7/2012 | Rivera | 227/177.1 |
| 8,240,538 B1 | 8/2012 | Manoux | 227/178.1 |
| 8,261,958 B1 | 9/2012 | Knodel | 227/176.1 |
| 8,353,930 B2 * | 1/2013 | Heinrich et al. | 606/219 |
| 8,365,971 B1 * | 2/2013 | Knodel | 227/175.1 |
| 8,397,973 B1 | 3/2013 | Hausen | 227/176.1 |
| 8,403,956 B1 * | 3/2013 | Thompson et al. | 606/219 |
| 8,453,904 B2 * | 6/2013 | Eskaros et al. | 227/175.1 |
| 8,469,253 B1 | 6/2013 | Knodel et al. | 227/176.1 |
| 8,475,491 B2 * | 7/2013 | Milo | 606/213 |
| 8,631,990 B1 * | 1/2014 | Park et al. | 227/175.2 |
| 8,631,992 B1 | 1/2014 | Hausen et al. | 227/179.1 |
| 8,662,369 B1 | 3/2014 | Manoux et al. | 227/175.1 |
| 8,985,427 B1 * | 3/2015 | Manoux et al. | 227/175.1 |
| 2001/0044656 A1 * | 11/2001 | Williamson et al. | 623/2.11 |
| 2003/0120284 A1 | 6/2003 | Palacios et al. | |
| 2003/0236551 A1 | 12/2003 | Peterson | |
| 2005/0033329 A1 * | 2/2005 | Bombard et al. | 606/153 |
| 2005/0070935 A1 * | 3/2005 | Ortiz | 606/153 |
| 2005/0075657 A1 * | 4/2005 | Bombard et al. | 606/153 |
| 2005/0131428 A1 * | 6/2005 | Bombard et al. | 606/139 |
| 2005/0184121 A1 | 8/2005 | Heinrich | |
| 2005/0203551 A1 * | 9/2005 | Weadock et al. | 606/153 |
| 2005/0242149 A1 * | 11/2005 | Higuchi | 227/2 |
| 2006/0011699 A1 | 1/2006 | Olson et al. | |
| 2006/0041273 A1 | 2/2006 | Ortiz et al. | |
| 2006/0085017 A1 * | 4/2006 | Borghi | 606/153 |
| 2006/0151567 A1 | 7/2006 | Roy | |
| 2006/0241660 A1 | 10/2006 | Bombard et al. | |
| 2006/0253143 A1 | 11/2006 | Edoga | |
| 2007/0027472 A1 | 2/2007 | Hiles et al. | |
| 2007/0034668 A1 | 2/2007 | Holsten et al. | |
| 2007/0073341 A1 | 3/2007 | Smith et al. | |
| 2007/0083234 A1 | 4/2007 | Shelton, IV et al. | |
| 2007/0114261 A1 * | 5/2007 | Ortiz et al. | 227/175.1 |
| 2007/0118163 A1 | 5/2007 | Boudreaux et al. | |
| 2007/0125828 A1 | 6/2007 | Rethy et al. | |
| 2007/0175950 A1 | 8/2007 | Shelton et al. | |
| 2007/0244558 A1 * | 10/2007 | Machiraju | 623/2.18 |
| 2008/0078807 A1 | 4/2008 | Hess et al. | |
| 2008/0082124 A1 * | 4/2008 | Hess et al. | 606/219 |
| 2008/0082126 A1 * | 4/2008 | Murray et al. | 606/221 |
| 2008/0272175 A1 | 11/2008 | Holsten et al. | |
| 2009/0001130 A1 * | 1/2009 | Hess et al. | 227/180.1 |
| 2009/0005809 A1 * | 1/2009 | Hess et al. | 606/220 |
| 2009/0065552 A1 * | 3/2009 | Knodel et al. | 227/180.1 |
| 2009/0177277 A1 * | 7/2009 | Milo | 623/2.36 |
| 2009/0188964 A1 * | 7/2009 | Orlov | 227/175.3 |
| 2010/0019014 A1 * | 1/2010 | Rodenhouse | 227/32 |
| 2010/0155453 A1 * | 6/2010 | Bombard et al. | 227/176.1 |
| 2010/0179559 A1 | 7/2010 | Walker | |
| 2010/0191255 A1 * | 7/2010 | Crainich et al. | 606/142 |
| 2010/0191282 A1 * | 7/2010 | Harris et al. | 606/219 |
| 2010/0256675 A1 * | 10/2010 | Romans | 606/219 |

(56) References Cited

U.S. PATENT DOCUMENTS

2011/0194914 A1* 8/2011 Kunz et al. .................... 411/443
2011/0278343 A1* 11/2011 Knodel et al. ............. 227/176.1
2012/0074202 A1* 3/2012 Knodel ...................... 227/180.1

FOREIGN PATENT DOCUMENTS

| | | |
|---|---|---|
| EP | 1736104 | 3/2009 |
| JP | 2005160933 | 6/2005 |
| RU | 2080833 | 6/1997 |
| WO | WO-81/01953 | 7/1981 |
| WO | WO-85/01427 | 4/1985 |

OTHER PUBLICATIONS

Lim, Jyue B., "Type Synthesis of a Complex Surgical Device", *Masters Thesis*, (Feb. 21, 2001).

Lim, Jonas J., et al., "Application of Type Synthesis Theory to the Redesign of a Complex Surgical Instrument", *Journal of Biomechanical Engineering* (124), (Jun. 2004),265-272.

Kolios, Efrossini et al., "Microlaparoscopy", *J. Endourology* 18(9), (Nov. 2004),811-817.

Steichen, Felicien M., et al., "Mechanical Sutures in Surgery", *Brit. J. Surg.* 60(3), (Mar. 1973),191-197.

* cited by examiner

CIRCULAR STAPLER

FIELD OF THE INVENTION

The invention generally relates to surgical instruments, and more specifically to circular surgical staplers.

BACKGROUND

Minimally invasive surgery is performed through small incisions in the body, into which trocar ports may or may not be placed. One or more surgical instruments are inserted through each incision in order to perform the surgical procedure. In order to effectuate one of the objectives of minimally invasive surgery, which is the minimization of incisions to the body to reduce healing time and scarring, it is desirable to minimize the number of incisions made in the body. The number of incisions and their placement are determined by the particular surgical procedure to be performed and the configuration of the instruments used to carry out that procedure. Circular staplers are often used in intestinal surgery and may be introduced transanally as part of a natural orifice translumenal endoscopic surgical (NOTES) procedure.

BRIEF DESCRIPTION OF THE DRAWINGS

The use of the same reference symbols in different figures indicates similar or identical items.

DETAILED DESCRIPTION

U.S. Patent Application Publication No. 2009/0065552, published on Mar. 12, 2009 (the "Endocutter Document"), is hereby incorporated by reference herein in its entirety.

Figure 1:
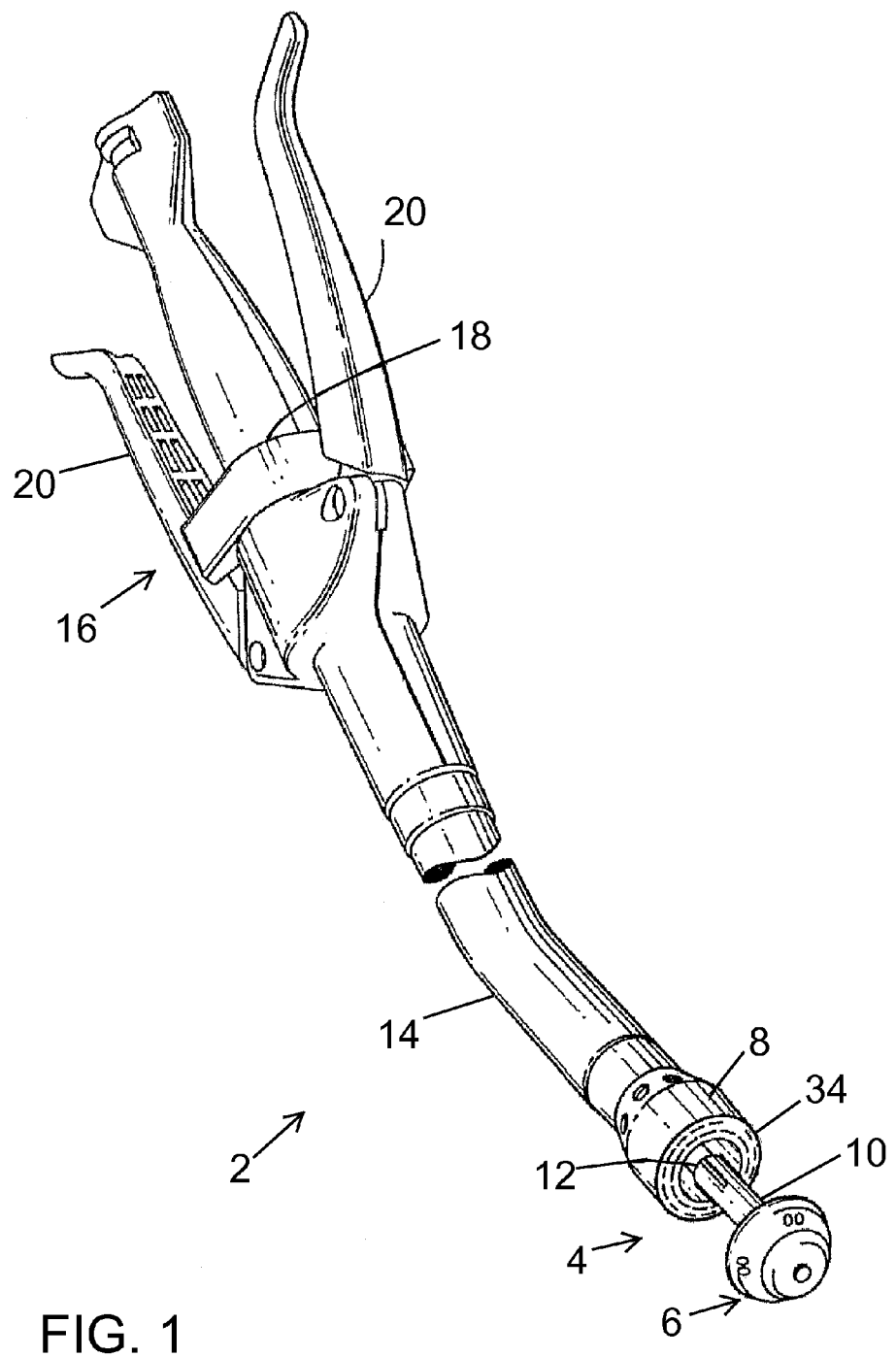
FIG. 1 is a perspective view of a circular stapler.

Referring to FIG. 1, an exemplary circular stapler 2 may include an end effector 4, which in turn includes a staple holder 8 and an anvil 6. The anvil 6 may include a rod 10 extending proximally therefrom into an aperture 12 in the staple holder 8. The anvil 6 may be detachable from the staple holder 8 by sliding the rod 10 out of the aperture 12, as is standard in the art. In this way, tissue can be sutured or otherwise connected to the anvil 6 temporarily, also as is standard in the art. A shaft 14 may extend proximally from the staple holder 8. The shaft 14 may be rigid along part or all of its length, and/or may include an articulating region, such as described in U.S. patent application Ser. No. 12/400,760, filed on Mar. 9, 2009 (the "Articulation Document"), which is hereby incorporated by reference in its entirety.

A handle 16 may be attached to the proximal end of the shaft 14, or any other suitable portion of the shaft 14. The shaft 14 may be fabricated integrally with the handle 16. Alternately, the shaft 14 and the handle 16 may be two separate items that are connected together in any suitable manner. The handle 16 may include any mechanism, mechanisms, structure or structures that are suitably configured to actuate the end effector 4. The handle 16 may be actuated purely by hand, meaning that the handle 16 mechanically converts force applied thereto by hand to force utilized to actuate the end effector 4. As another example, the handle 16 may include a source of stored energy for actuating the end effector 4. The source of stored energy may be mechanical (such as a spring), electrical (such as a battery), pneumatic (such as a cylinder of pressurized gas) or any other suitable source of stored energy. The source of stored energy, its regulation, and its use in actuating the end effector 4 may be as described in commonly-assigned U.S. Pat. No. 7,682,368, issued on Mar. 23, 2010, which is herein incorporated by reference in its entirety. The handle 16 may instead, or also, include a connector or connectors suitable for receiving stored energy from an external source, such as a hose connected to a hospital utility source of pressurized gas or of vacuum, or an electrical cord connectable to a power source. The handle 16 may include two opposed handgrips 18 that can be squeezed together to deploy staples from the staple holder 8. As another example, the handle 16 may be arranged in any manner that allows for control of staple deployment. The handle 16 may also include provisions for affirmative clamping of the anvil 6 to the staple holder 8. Where the rod 10 is substantially freely slidable into the aperture 12 in the staple holder 8, the handle 16 may include a control 18 that may rotate to apply torque or other clamping force that is transmitted through the shaft 14 in any suitable manner to hold the rod 10 in place. Alternately, the rod 10 may extend up the shaft 14 into the handle 16, and may be threaded to correspond with the control 18, such that the control 18 may be screwed onto the rod 10 or otherwise associated with the rod 10 in order to hold the rod 10 such that the anvil 6 is clamped against the staple holder 8.

Figure 2:
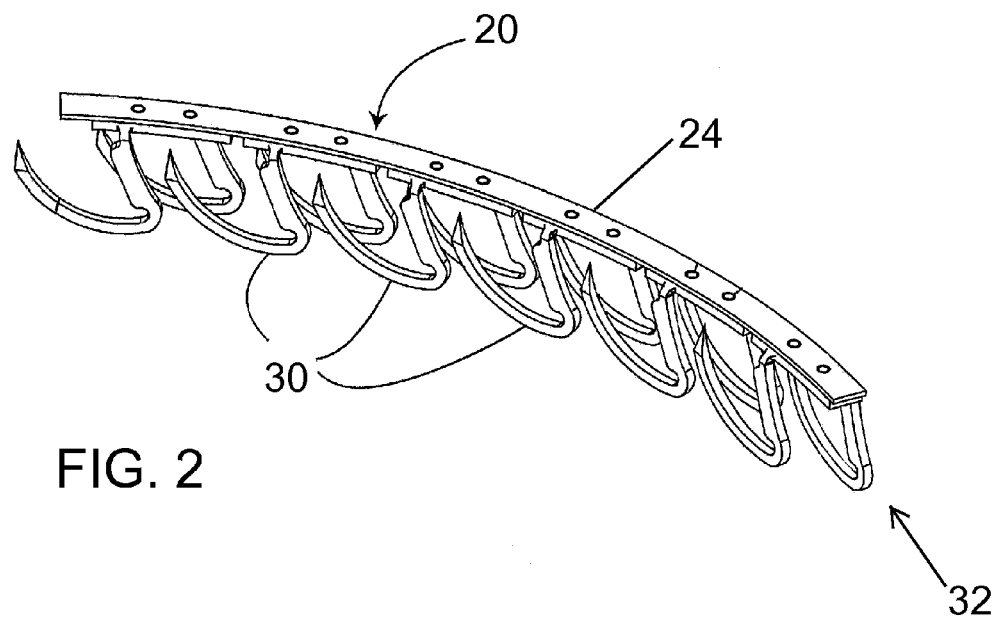
FIG. 2 is a perspective view of an arcuate section of a feeder belt ring.

Referring also to FIG. 2, a feeder belt ring 22 may be positioned in the staple holder 8. The feeder belt ring 22 may be fabricated generally as set forth in U.S. patent application Ser. No. 11/851,379, filed Sep. 6, 2007; U.S. patent application Ser. No. 11/956,988, filed Dec. 14, 2007; and U.S. patent application Ser. No. 12/263,171, filed Oct. 31, 2008 (the "Endocutter Documents"), which are herein incorporated by reference in their entirety. The difference between the feeder belt of the Endocutter Documents and the feeder belt ring 22 is described here, in the interest of brevity. The feeder belt ring 22 is arranged in a ring formation with an outer diameter 24 and an inner diameter 26. Inside the inner diameter 26 is a circular aperture 28. The feeder belt ring 22 may be a long, narrow, thin strip of material from which one or more staples 30 extend. At least one staple 30 may be integral with the feeder belt 90, and frangibly connected to the feeder belt 90 at one end, with the other end of the staple being free. One row 32 of staples 30 may be located along each side of the feeder belt ring 20. The feeder belt ring 22 may be fixed to the staple holder 8, and aligned with the staple apertures 34 in the staple holder 8 such that the staples 30 are substantially aligned with the staple apertures. The feeder belt ring 22 may be permanently affixed to the staple holder 8, such as by welding. As another example, the feeder belt ring 22 may be interchangeably fixed to the staple holder 8, such as by a pressure fit, by clips, or in any other manner that allows the feeder belt ring 22 to be swapped out for a fresh feeder belt ring 22, as described in greater detail below.

Figure 4:
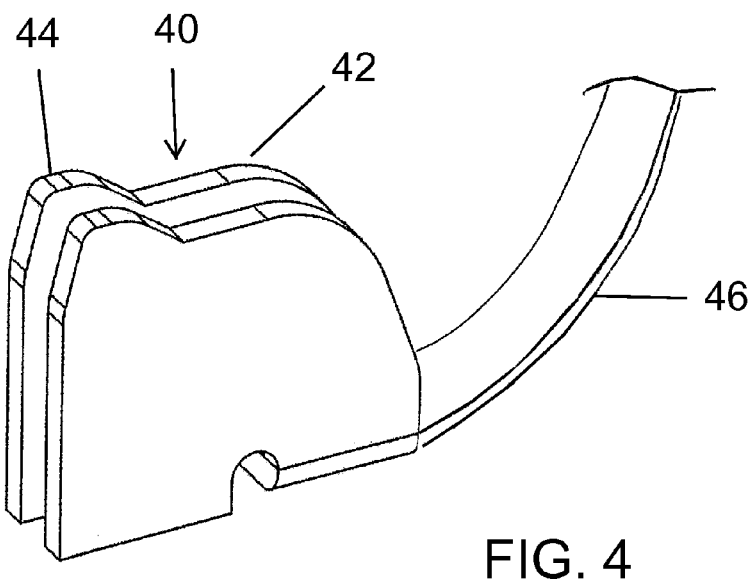
FIG. 4 is a perspective view of an arcuate section of an exemplary wedge ring and wedge.
Figure 5:
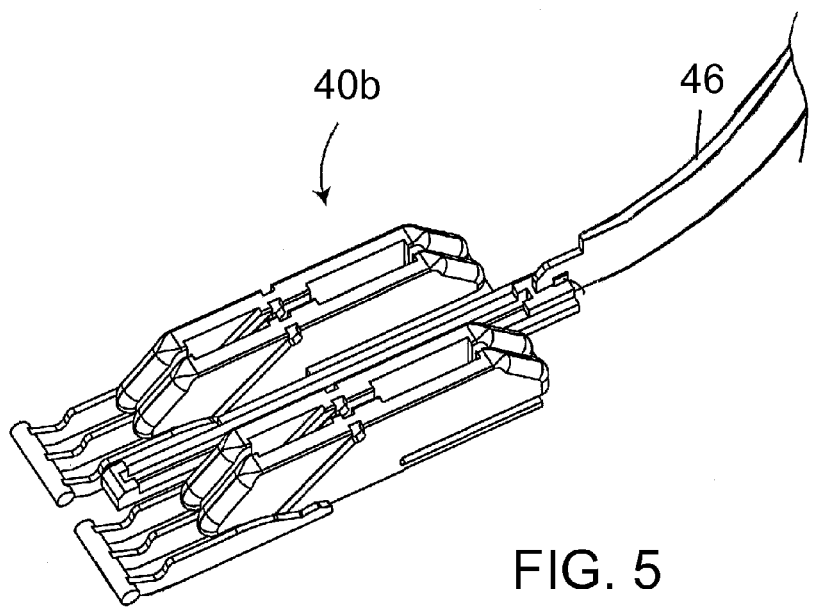
FIG. 5 is a perspective view of an arcuate section of a different exemplary wedge ring and wedge.

Referring also to FIG. 4, an exemplary wedge 40 is shown. The wedge 40 may be shaped generally as set forth in the Endocutter Documents. The wedge 40 may have a shape that facilitates deployment of the staples 30 The wedge 40 may have a first segment 42 shaped to facilitate deployment of a staple 30, and a second segment 44 shaped to facilitate shearing or otherwise separating a staple 30 from the feeder belt 20. The first segment 42 is curved upward and distally; the curve may have any shape that facilitates formation of a staple 30. The second segment 44 also may be curved upward and distally; the curve may have any shape that facilitates breaking of a staple 30 from the feeder belt ring 22. By providing two distinct segments 42, 44 on the wedge 40, formation and separation of each staple 30 can be separately controlled. The wedge 40 may be located at an end of a wedge ring 46. As another example, the wedge 40 may be positioned on the surface of a wedge ring 46. The wedge ring 46 may be a complete ring, or may be an arcuate section thereof. The wedge ring 46 may be generally rigid. The wedge ring 46 is coupled to the handle 16 in a manner that allows the handle 16 to rotate the wedge ring 46 about the longitudinal axis of the staple holder 8. The wedge ring 46 may be positioned between the feeder belt ring 22 and the distal surface of the staple holder 8 in which the staple apertures 34 are defined. Alternately, the wedge ring 46 may be positioned differently in the staple holder 8. Multiple wedges 40 may be positioned on the wedge ring 46. The amount of rotation required for the wedges 40 to deploy and shear off all of the staples 30 decreases with the number of wedges 40 used, as described in greater detail below.

Figure 3:
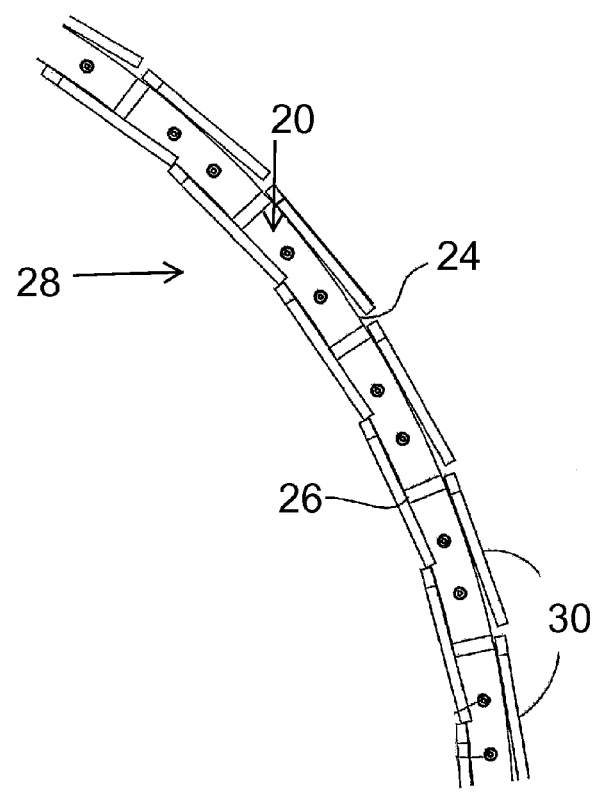
FIG. 3 is a perspective cutaway view of a mode button of the stapler of FIG. 1.

Referring also to FIG. 4, a different exemplary wedge 40b is shown. The wedge 40b may be an active wedge, such as set forth in U.S. patent application Ser. No. 13/090,214, filed on Apr. 19, 2011, which is herein incorporated by reference in its entirety. The wedge 40b may be located at an end of a wedge ring 46b. The wedge ring 46b may be oriented generally vertically, as seen in FIG. 4, rather than horizontally as seen in FIG. 3. Alternately, the wedge ring 46b may be simply a wire fixed to one end of the wedge 40b. The wedge ring 46b is coupled to the handle 16 in a manner that allows the handle 16 to rotate the wedge ring 46b about the longitudinal axis of the staple holder 8. The wedge ring 46b may be positioned between the feeder belt ring 22 and the distal surface of the staple holder 8 in which the staple apertures 34 are defined. Alternately, the wedge ring 46b may be positioned differently in the staple holder 8. Multiple wedges 40 may be positioned on the wedge ring 46b. The amount of rotation required for the wedges 40 to deploy and shear off all of the staples 30 decreases with the number of wedges 40 used, as described in greater detail below.

Operation

The end effector 4 is positioned such that tissue is located between the anvil 6 and staple holder 8, in any suitable manner. The anvil 6 and staple holder 8 are then clamped together, such as described above. That is, the anvil 6 and/or staple holder 8 are moved longitudinally relative to one another, and held in place relative to one another, so that tissue held therebetween is compressed to a desired degree. The handle 16 is actuated in any suitable way to do so, such as by actuating the control 18.

With tissue held in place, the handle 16 may then be actuated to deploy staples 30 into tissue. As set forth above, the handgrips 20 may be squeezed, transmitting force through one or more wires, rods, springs, gears, or other or additional mechanisms. The actuation of the handgrip 20 causes the wedge ring 46 to rotate within the staple holder 8. The feeder belt ring 22 is located in the staple holder 8 such that the staples 30 are located closer to the staple apertures 34 than the feeder belt ring 22. As the wedge ring 46 rotates, it sequentially encounters staples 30, and sequentially deploys, then breaks off from the feeder belt ring 22, staples 30 in each row. The deployment and shearing process is described in detail in the Endocutter Documents. As the staples 30 are deformed, they are urged through the corresponding apertures 34 in the staple holder 8, then ejected through those apertures 34 after they are fully formed and then broken from the feeder belt ring 22. Where a single wedge 40 is used, the wedge ring 46 is rotated substantially 360° in order to deploy and break off all of the staples 30. Where two wedge rings 46 are used, the wedge ring 46 is rotated substantially 180° in order to deploy and break off all of the staples 30. Consequently, it will be appreciated that the wedge ring 46 is rotated a number of degrees substantially equal to 360° divided by the number of wedges 40 utilized. Where the wedge 40b is used, the wedge 40b is moved into active mode before deploying staples, substantially as set forth in U.S. patent application Ser. No. 13/090,214. After the staples 30 are deployed and broken from the feeder belt ring 22, they are arranged in two or more substantially concentric rings in tissue.

As another example, the wedge ring 46 is not used, and compression of the staples 30 against the anvil 6 during clamping causes deformation of the staples 30. The staples 30 may be broken off the feeder belt ring 22 in another manner, or may remain on the feeder belt ring 22. In some surgical applications, it may be desirable to deploy the feeder belt ring 22 into the patient along with the staples 30. If so, the feeder belt ring 22 and/or staples 30 may be fabricated from resorbable material such as but not limited to polyglycolic acid. Whether or not the feeder belt ring 22 is deployed into tissue, the staples 30 may be fabricated from resorbable material such as but not limited to polyglycolic acid.

Optionally, the end effector 4 may then incise the tissue clamped between the anvil 6 and staple holder 8 using a circular knife (not shown) held within either or both of the anvil 6 and staple holder 8, as is known in the art. The end effector 4 then may be unclamped, releasing tissue held within. The circular stapler 2 then may be removed from the patient. Optionally, the stapler holder 8 may be reloaded with a new feeder belt ring 22. For example, the spent feeder belt ring 22 may be removed from the staple holder 8 with a forceps or other tool, or may be shaken out of the staple holder 8, or may be removed from the staple holder 8 in any other suitable manner. Afterwards, a fresh feeder belt ring 22 may be placed in the staple holder 8 in any suitable manner. Alternately, the staple holder 8 as a whole may be interchangeable for a new staple holder 8 after firing.

The operation of the circular stapler 2 may be carried out in the course of testing at a factory or other location. If so, the user that possesses the circular stapler 2 may be a technician, machine or text fixture that exercises the surgical stapler 2 in the course of testing. The term "tissue," in the context of testing the circular stapler 2 only, includes any substance or material used as a substitute for tissue in the course of testing.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. The use of terms such as "upward" and "downward" in this document refers to the orientation of parts on the page for descriptive clarity, and in no way limits the orientation of the device in use. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. Therefore, the invention is not to be restricted or limited except in accordance with the following claims and their legal equivalents.

What is claimed is:

1. A circular stapler, comprising:
   an anvil;
   a staple holder connected to said anvil; and
   a feeder belt ring held within said staple holder, said feeder belt ring including a plurality of staples frangibly affixed thereto, the staple holder configured to hold the plurality of staples about a longitudinal axis of a shaft coupled to the anvil, each of the plurality of staples extending parallel to the longitudinal axis.

2. The surgical apparatus of claim 1, wherein said feeder belt ring defines a circular aperture at the center thereof.

3. The surgical apparatus of claim 1, further comprising a wedge ring rotatable relative to said feeder belt ring, and a wedge connected to said wedge ring, wherein rotation of said wedge ring and said wedge deploys and then breaks off at least one said staple from said feeder belt ring.

4. The surgical apparatus of claim 3, wherein said wedge is an active wedge.

5. The surgical apparatus of claim 3, wherein said rotation is substantially 360 degrees.

6. The surgical apparatus of claim 1, wherein at least two separate rows of said staples extend from said feeder belt ring.

7. The circular stapler of claim 1, further comprising a wedge configured to separate each of the plurality of staples from the feeder belt ring.

8. The circular stapler of claim 1, further comprising a wedge ring and a wedge, the wedge ring configured to pull the wedge along a circular path defined by the wedge ring, so as to deploy the plurality of staples.

9. The circular stapler of claim 1, a wedge ring coupled to a wedge, the wedge ring defining a circle concentric with the feeder belt ring.

10. A surgical stapler, comprising:
    an anvil;
    a staple holder coupled to said anvil, the staple holder configured to hold a plurality of staples in a ring formation about a longitudinal axis of a shaft coupled to the anvil, each of the plurality of staples extending parallel to the axis; and
    a wedge movably coupled to the staple holder so that the wedge rotates around the longitudinal axis to deploy the plurality of staples in a sequential manner around the longitudinal axis.

11. The surgical stapler of claim 10, further comprising a wedge ring coupled to the wedge, the wedge ring centered on the axis.

12. The surgical stapler of claim 10, wherein the wedge is configured to separate each of the plurality of staples from the staple holder.

13. The surgical stapler of claim 10, further comprising a feeder belt ring having the plurality of staples frangibly attached thereto.

14. The surgical stapler of claim 10, wherein the wedge is positioned at a predetermined radius from the axis and is configured to travel about the axis at the predetermined radius.

15. The surgical stapler of claim 10, further comprising a wedge ring, with the wedge coupled to the wedge ring, wherein the wedge ring rotates about the axis.

16. A surgical apparatus, comprising:
    a shaft, having a longitudinal axis;
    an anvil coupled to the shaft;
    a staple holder coupled to the shaft, the staple holder configured to hold a plurality of staples in a feeder belt ring about the longitudinal axis, each of the plurality of staples extending parallel to the longitudinal axis; and
    a wedge movably coupled to the shaft so that the wedge circulates about the longitudinal axis to detach the plurality of staples from the feeder belt ring in a sequential manner around the longitudinal axis.

17. The surgical apparatus of claim 16, further comprising a wedge ring coupled to the wedge, wherein the wedge ring includes one of: a complete ring; or an arcuate section of a ring.

18. The surgical apparatus of claim 16, wherein the wedge includes a plurality of wedges.

19. The surgical apparatus of claim 16, wherein the wedge controls formation and separation of each of the plurality of staples.

20. The surgical apparatus of claim 16, further comprising a wedge ring coupled to the wedge, wherein the wedge includes a plurality of wedges and wherein rotation of the wedge ring about the axis by less than or equal to 180 degrees deploys and breaks off all of the plurality of staples.

* * * * *